United States Patent [19]

Maeda et al.

[11] Patent Number: 5,100,671
[45] Date of Patent: Mar. 31, 1992

[54] COATING MATERIAL FOR MEDICAL CARE

[75] Inventors: Karo Maeda, Mezon Tamate#402, No. 102, Yamatecho, Naka-ku, Yokohama City Kanagawa Pref.; Satoshi Ando, Osaka, both of Japan

[73] Assignee: Karo Maeda, Yokohama, Japan

[21] Appl. No.: 213,632

[22] Filed: Jun. 30, 1988

[30] Foreign Application Priority Data

Jul. 9, 1987 [JP] Japan .................. 62-171722

[51] Int. Cl.⁵ ................................. A61F 13/00
[52] U.S. Cl. ................................. 424/443; 424/444; 424/445; 424/446; 523/111
[58] Field of Search ................ 424/443–446, 424/79; 523/111

[56] References Cited

U.S. PATENT DOCUMENTS

| | | | |
|---|---|---|---|
| 2,550,489 | 4/1951 | Martin | 424/79 |
| 3,983,053 | 9/1976 | Courtney | 424/79 |
| 4,486,488 | 12/1984 | Pietsch | 424/443 |
| 4,742,164 | 5/1988 | Iguchi et al. | 435/823 X |
| 4,766,229 | 8/1988 | Kobayashi et al. | 556/138 |
| 4,801,445 | 1/1989 | Fukui | 424/69 |

FOREIGN PATENT DOCUMENTS 0298726 1/1989 European Pat. Off.

OTHER PUBLICATIONS

Patent Abstracts of Japan, vol. 12, No. 47 (C-475) [2894], 12th Feb. 1988, p. 109 C 475; & JP-A-62 195 037 (Kanebo Ltd).
Patent Abtracts of Japan, vol. 10, No. 17, (C-324)[2074], 23rd Jan. 1986, p. 159 C 324; & JP-A-1784 707 (Kanebo K.K.).
Patent Abstracts of Japan, vol. 10, No. 23 (C-325)[2080], 26th Jan. 1986, p. 163 C 325; & JP-A-60 178 810 (Kanebo K.K.).
Patent Abstracts of Japan, vol. 10, No. 335 (C-384) [2391], 13th Nov. 1986, p. 42 C 84; & JP-A-61 138 658 (Kanebo Ltd).
Patent Abstracts of Japan, vol. 10, No. 28 (C-326) [2085], 4th Feb. 1986; 7 JP-A-60 181 002 (Kanebo K.K.).
Patent Abstracts of Japan, vol. 10, No. 350 (C-387) [2406], 26 Feb. 1988, p. 86 C 387; & JP-A-61 151 131 (Lion Corp.).

Primary Examiner—Thurman K. Page
Attorney, Agent, or Firm—Oblon, Spivak, McClelland, Maier & Neustadt

[57] ABSTRACT

A coating material for medical care having anti-bacterial action against *Psuedomonas aeruginosa, Staphylococcus aureus, Escherichia coli* and fungus is disclosed.

Powdered zeolite, wherein one or the whole of metals contained in said zeolite is substituted by at least one kind of ion exchangeable metal selected from the group consisting of Ag, Cu and Zn, is coated onto the coating material made of silicone rubber etc or kneaded thereinto.

5 Claims, 1 Drawing Sheet

1

COATING MATERIAL FOR MEDICAL CARE

BACKGROUND OF THE INVENTION

1. FIELD OF THE INVENTION

The present invention relates to a coating material for medical care ; and more particularly relates to an anti-bacterial coating material for medical care against pseudomonas aeruginosa for coating the affected part of the skin ascribable to burn or wound.

2. Discussion of the Background

Conventionally, a great variety of organometallic compounds or organic compounds were known as an anti-bacterial agent. However, said compounds have in general low melting points and also high volatility, thus rendering said compounds thermally unstable so as to cause early deterioration of the effectiveness therreoof when those are employed in preparing a coating material for medical care having anti-bacterial action. Therefore, such compounds as above have not conventionally been employed as a coating material for medical care in view of such inconveniences as deteriorative effectiveness of anti-bacterial action, side effects, stimulant and short-period effectiveness.

OBJECT AND SUMMARY OF THE INVENTION

In order to provide a coating material for medical care for coating the affected part of the skin ascribable to burn or wound having anti-bacterial action against aeruginosa or staphylococcus aureus, which have the close relationship with burn etc, the inventor of the present patent application has found after years of study that anhydrous or hydrated powdered anti-bacterial compound, wherein one or all of metals contained in zeolite are substituted by at least one kind of ion exchangeable metals selected from the group consisting of Ag,Cu and Zn, have anti-bacterial action against pseudomonas aeruginosa and staphylococcus aureus.

The aforementioned anti-bacterial compound was conventionally known as an anti-bacterial agent employed in the production of architectual products on wall surfaces or building materials, e.g. disclosed in Japanese patent laidopen publication No. 181002/1985, but it was not clear that said anti-bacterial compound could be applicable to the field of medical care.

With the above in mind, it is an object of the present invention to provide a coating material for medical care having anti-bacterial action.

The aforementioned object of the present invention can be attained by providing a coating material for medical care comprising powdered zeolite, wherein one or all of metals contained in said zeolite is substituted by at least one kind of ion exchangeable metals selected from the group consisting of Ag,Cu and Zn, being coated onto at least one side of the outer surfaces of the coating material made of silicone rubber in the form of a film or kneaded thereinto.

The present invention was achieved by paying attention to the fact that the aforementioned compound acts as a long time anti-bacterial effect to moisture or water, and the gist thereof resides in that the coating material for medical care coated with the aforementioned anti-bacterial compound onto the outer surface thereof is applied to the wound ascribable to burn or said compound is kneaded into said coating material made of silicone rubber or the others ( hereinafter described in detail ) to constitute said coating material so as to apply the same to the burn from which secretion comes out.

Accordingly, said anti-bacterial compound continues to generate Ag ion,Cu ion and Zn ion for a long time when said compound comes in contact with the secretion and owing to the catalysis thereof anti-bacterial effect continues against pseudomonas aeruginosa, staphylococcus aureus, escherichia coli and fungus, for example.

Furthermore, said compound is thermally stable to the body heat and is safe as inorganic substance so that it is effective as a coating material for medical care.

BRIEF DESCRIPTION OF THE DRAWINGS

In the FIGS.

Among said FIGS., FIG. 1 is a perspective view of said coating material for medical care.

FIG. 2 is a sectional view taken along line 11-11 in FIG. 1, and

FIG. 3 is a sectional view of another embodiment of the present invention wherein the coating material according to the present invention is laminated in the form of sandwiches by employing the same or at least two different materials as the base thereof.

DETAILED DESCRIPTION OF THE PREFERRED EMBODIMENTS

Hereinafter, embodiments according to the present invention will be described in detail with reference to the drawings.

Figure 1:
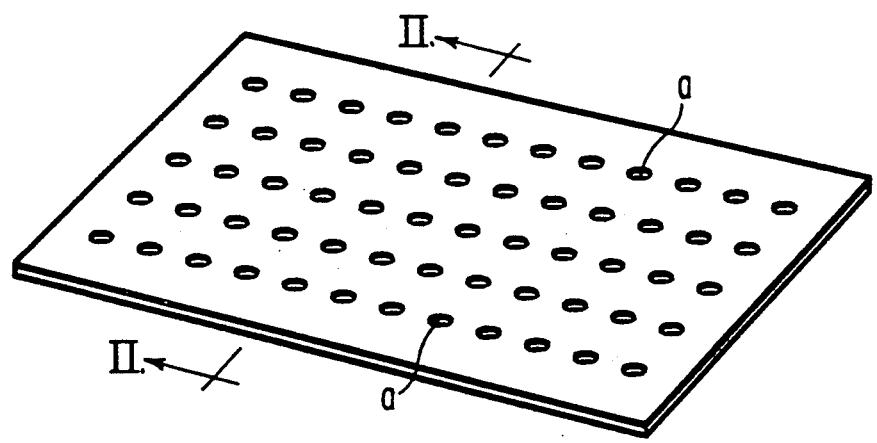
FIG. 1 to FIG. 3 show one embodiment according to the present invention, wherein the present invention is applied to a coating material for medical care.
Figure 2:
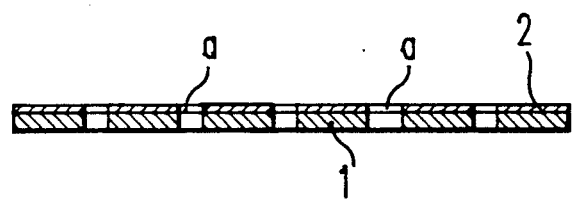

FIG. 1 is a coating material for medical care for coating the affected part of the skin ascribable to a wound or burn. In the drawing, (1) is a coating material and said coating material (1) may be made of silicone rubber in the form of a film or net so as to easily coat the anti-bacterial compound according to the present invention thereonto. As illustrated in FIG. 2, onto both surfaces of said coating material or one side surface thereof, i.e. the surface directly applied to the affected part of the skin, said anti-bacterial compound is coated by means of conventional adhesives.

In FIG. 2, (2) is a coated layer with the anti-bacterial compound and (a) is a through hole and secretion generated from the affected part of the skin is discharged out of said hole (a).

Onto the outer surface of said coating material (1), the anti-bacterial compound is coated as illustrated in FIG. 2, but it is optional to prepare the coating material by kneading said compound into the solution for molding said coating material in molding the same so as to prepare the material itself.

Of course, said coating material may be prepared without forming the through hole(a) and the number and size of said holes may also be optional Furthermore, said coating material may be prepared by kneading the aforementioned compound into synthetic resins, amino acid, collagen, chitin, natural leather, or chemically synthesized or natural fiber as the base thereof in lieu of employing silicone rubber. Regarding the quantity of said anti-bacterial compound , it is optional and not particularly specified.

The aforementioned anti-bacterial compound is anhydrous or hydrated natural or synthesized zeolite or both, wherein one or the whole of the metals contained in said zeolite is substituted by at least one kind of ion exchangeable metals selected from the group consisting of Ag, Cu and Zn.

Figure 3:
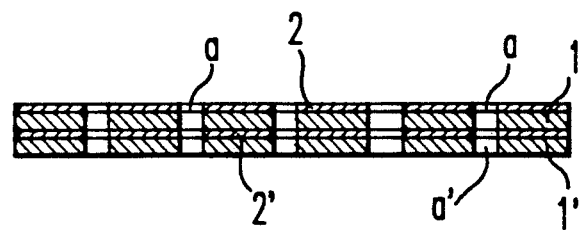

Instead of silicone rubber as the base of the coating material according to the present invention, it may employ amino acid, collagen, chitin, synthetic resins, natural leather, or natural or chemically synthesized fiber as the base thereof. The coating material may also be employed in the form of sandwiches by employing at least two different or the same kinds of the coating material as above described as illustrated in FIG. 3, wherein (1') is a coating material prepared, for example, by employing synthetic resins as the base thereof instead of silicone rubber laminated with the coating material(1) in the form of sandwiches and (2') is a coated layer of the antibacterial compounds and further (a') is a through hole.

As is clear from the above, since the coating material for medical care according to the present invention comprised anhydrous or hydrated powdered anti-bacterial compound as described above being coated onto at least one side of the outer surfaces of said coating material made of silicone rubber for example or kneaded thereinto in preparing the same, said compound exhibits strong anti-bacterial action against pseudomonas aerugiuosa, staphylococcus aureus, escherichia coli and fungus without causing any inflammatory change of the skin when the coating material is applied to the affected part of the skin ascribable to burn or wound.

Furthermore, since said anti-bacterial compound continues anti-bacterial effect for a long time when said compound comes in touch with secretion etc, it is not necessary to replace the coating material in use by the new one as often observed in employing a conventional coating material for medical care, thereby considerably reducing trouble ascribable thereto.

In employing silicone rubber and the like, it has such advantage as being able to employ the same repeatedly after washing even when a coating material for medical care thus prepared is contaminated by blood or secretion.

Furthermore, the anti-bacterial compound is thermally stable to body heat and also has no toxicity so as to employ the same safely.

Thus, the present invention can provide an effective and safe coating material for medical care having anti-bacterial action as described above.

What is claimed is:

1. A medical article having a base material selected from the group consisting of amino acids, collagen, chitin, synthetic resins, natural leather, natural and chemically synthesized fibers, coated on at least one side of its outer surfaces with an antibacterially effective amount of a metal ion-coating zeolite, said zeolite containing at least one ion selected from the group consisting of Ag, Cu and Zn ions.

2. A medical article, wherein said article comprises a base material selected from the group consisting of amino acids, collagen, chitin, synthetic resins, natural leather, natural and chemically synthesized fibers, coated on at least one side of its outer surfaces with an antibacterially effective amount of a film of a metal ion-containing zeolite, or wherein a metal ion-containing zeolite is kneaded into at least one side of the outer surface of said medical article; wherein said metal ion-containing zeolite contains at least one ion selected from the group consisting of Ag, Cu and Zn ions.

3. The medical article of claim 1, wherein said metal-containing zeolite coated on at least one side of the outer surfaces of said article is present in the form of a net.

4. The medical article of claim 2, wherein said film comprises a plurality of holes therethrough.

5. The medical article of claim 4, wherein said metal-containing zeolite coat is sandwiched between said outer surface and a covering substrate.

* * * * *